Figure 1:
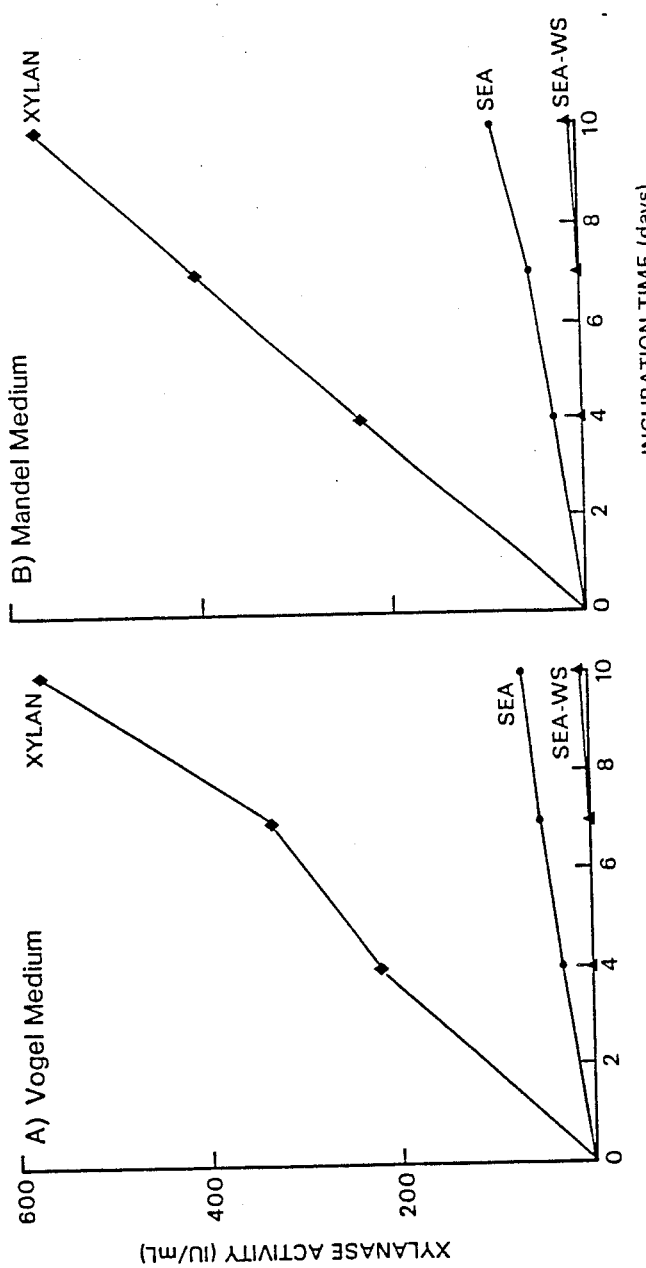

United States Patent [19]

Yu et al.

[11] Patent Number: 4,966,850
[45] Date of Patent: Oct. 30, 1990

[54] PRODUCTION OF THERMOSTABLE XYLANASE AND CELLULASE

[75] Inventors: Ernest K. C. Yu, Brampton; Larry U. L. Tan, Navan; John N. Saddler, Ottawa, all of Canada

[73] Assignee: Forintek Canada Corp., Ottawa, Canada

[21] Appl. No.: 340,307

[22] Filed: Apr. 19, 1989

Related U.S. Application Data

[63] Continuation of Ser. No. 5,853, Jan. 21, 1987, abandoned.

[51] Int. Cl.$^5$ ............................ C12N 9/24; C12N 9/42
[52] U.S. Cl. ..................................... 435/200; 435/209; 435/814
[58] Field of Search ........................ 435/200, 209, 814

[56] References Cited

U.S. PATENT DOCUMENTS 4,725,544 2/1988 Tza et al. ............................. 435/200

OTHER PUBLICATIONS

Shepherd et al, Biochemical Journal, vol. 193, pp. 67–74 (1981).
ATCC Catalogue of FUNGI/YEASTS, 16th edition, 1984, p. 316.
McCarthy, Appl. Microbiol Biotechnol, vol. 21, pp. 238–244 (1985).
Tong, C. C., et al. (1980) Biochem. J. 191, 83–94.
"Evaluation of Spray-Drying Methods for Cellulase Preservation" by Himmel et al, Biotechnology and Bioengineering Symposium No. 17 (1986), 413–423.
"Comparative Study of Cellulases and Hemicellulases from Four Fungi: Mesophiles Trichoderma Reesei and Penicillium sp. and Thermophiles Thielavia Terrestris and Sporotrichum Cellulophilum" by Henri Durand et al, Enzyme Microbiology Technology, 1984, vol. 6, Apr., 175–180.
J. N. Saddler and M. Mes-Hartree, "The Enzymatic Hydrolysis and Fermentation of Pretreated Wood Substrates", Biotech Advs. vol. 2, pp. 161–181 (1984).
Ernest K. C. Yu, Lise Deschatelets and John N. Saddler, "The Combined Enzymatic Hydrolysis and Fermentation of Hemicellulose to 2,3-Butamediol", Applied Microbiology Biotechnology, 19, pp. 365–372 (1984).
E. K. C. Yu, L. Deschatelets and J. N. Saddler, "Combined Enzymatic Hydrolysis and Fermentation Approach to Butanediol Production from Cellulose and Hemicellulose Carbohydrates of Wood and Agricultural Residues", Biotechnology and Bioengineering Symp. No. 14, pp. 341–352 (1984).
E. K. C. Yu, L. Deschatelets, L. V. L. Tan and J. N. Saddler, "A Simple Method for Xylanase Preparation Used for the Hydrolysis and Fermentation of Hemicellulose to Butanediol", Biotech Lett 7, No. 6, pp. 425–430 (1985).
J. Woodward, "Xylanses: Functions, Properties and Applications", Introduction to Topics in Enzyme and Fermentation Biotechnology 8, pp. 8–30 (1984).
Robert F. H. Dekker and Geoffrey N. Richards, "Hemicellulases: Their Occurrence, Purification, Properties and Mode of Action", Adv. Carbohyd. Chem. Biochem 32, pp. 277–352 (1976).
Ernest K. C. Yu, Larry U. L. Tan, Maria K-H Chan, Lise Deschatelets and John N. Saddler, "Production of Thermostable Xylanase by a Thermophilic Fungus, Thermoascus Aurantiaeus", Enzyme Microb. Technol. 9, Yamary pp. 16–24 (1987).
D. L. Ristroph and A. E. Humphrey, "Kinetic Characterization of the Extdxracellular Xylanases of Ther- (List continued on next page.)

Primary Examiner—Elizabeth C. Weimar
Assistant Examiner—Charles L. Patterson, Jr.
Attorney, Agent, or Firm—Trevor C. Klotz

[57] ABSTRACT

The present invention provides for the use in the production of cellulolytic and xylanolytic enzymes, particularly xylanase and cellulase, of the microorganism Thermoascus aurantiacus in a culture medium containing at least one of a cellulose or hemicellulose substrate whereby to produce thermostable enzymes, particularly cellulase and xylanase.

14 Claims, 5 Drawing Sheets

OTHER PUBLICATIONS momonospora sp.", Biotech Bioeng XXVII, pp. 832-836 (1985).

Henri Durand, Philipe Soucaille and Gerard Tiraky, "Comparative Study of Cellulases and Hemicellulases from Four Fungi: Mesophiles Trichoderma Reesei and Penicillium sp. and Thermophiles Ticlavia Terrestris and Sporotrichum Cellulophilum", Enzyme Microb. Technol., 6 Apr., pp. 175-180 (1984).

Maheshwari et al, "Isolation and Culture of a Thermophilic Fungus, Melanocarpus albomyces and Factors Influencing the Production and Activity of Xylanase", J. Gen Microb. 131, pp. 3017-3027 (1985).

Jean-Francois Berenger et al, "Production, Purification and Properties of Thermostable Xylanase from Clostridium Stercorarium", Can. J. Microbiol. 31, pp. 635-643 (1985).

Hajime Yoshioka et al, "Purification and Properties of Thermostable Xylanase from Talaromyces byssochlamydiodes YH-50", Agric. Biol. Chem. 45 (11), pp. 2425-2432 (1981).

Michael R. Tansey, "Agar-Diffusion Assay of Cellulolytic Ability of Thermophilic Fungi", Cerch. Microbiol 787, pp. 1-11 (1971).

Robert F. Dekker et al, "Purification, Properties and Mode of Action of Hemicellulase II Produced by Ceratocyshs Paradoxa", Carbohydrate Research 42, pp. 107-123 (1975).

Wataru Okazaki et al, "Purification and Characterization of Xylanases from Alkalophilic Thermophilic Bacettus spp.", Agric. Biol. Chem. 49 (7), pp. 2033-2039 (1985).

Masaru Matsuo et al, "Properties of Xylanase of Malbranchea pulchella var. Sulfurea No. 48", Agric. Biol. Chem 49(3), pp. 839-841 (1985).

PRODUCTION OF THERMOSTABLE XYLANASE AND CELLULASE

This application is a continuation of application Ser. No. 005,853, filed Jan. 21, 1987, abandoned.

The present invention relates to the production of xylanolytic and cellulolytic enzymes and particularly xylanase and cellulase. In particular the present invention relates to the production of thermally stable xylanase and cellulase enzymes, particularly xylanase enzymes, by culturing a particular hemicellulolytic microorganism in a nutrient medium containing at least one cellulosic or hemicellulosic substrate.

Hemicelluloses constitute 20 to 35% by weight of wood and agricultural residues and serve as an abundant and inexpensive source of fermentable carbohydrates. Efficient utilization of hemicellulose of biomass will enhance the economic competitiveness of bioconversion processes which must compete with petrochemical processess. Recently it has been demonstrated the technical feasability of using the extracellular xylanases produced by *Trichoderma harzianum* and *Trichoderma reesei* for the hydrolysis or combined hydrolysis and fermentation of hemicelluloses. See for example Yu, E. K. C., Deschatelets, L. and Saddler, J. N., Appl. Microbiol. Biotechnol. 1984, 19, 365–372, Yu, E. K. C., Deschatelets, L. and Saddler, J. N., Biotechnol. Bioeng. Symp. 1984, 14, 341–352 and Yu, E. K. C., Deschatelets, L., Tan, L. U. L. and Saddler, J. N., Biotechnol. Lett. 1985, 7, 425–430. Thus the applicants are presently developing a process for the bioconversion of wood sugars to fuels and chemicals. The process is an integration of the steam pretreatment of wood residues, production of cellulase and xylanase enzymes, enzymatic hydrolysis of pre-treated wood cellulose and hemicelluloses with said enzymes to component sugars and subsequent fermentation of the sugars to produce a variety of fuels and chemicals. At present enzymatic hydrolysis step is carried out using non-thermostable cellulases and xylanases obtained from the culture filtrates of *Trichoderma harzianum* E58 from the Forintek Canada Corp. culture collection. Although the enzymes produced by the aforesaid fungus have numerous desirable qualities, the enzymatic hydrolysis step is still a bottleneck in the overall conversion scheme. This is in part due to the cost of producing the enzymes, the instability of the enzymes, particularly the xylanases, the low efficiency of the enzymatic hydrolysis which must be carried out at temperatures below 50° C. and the need to carry out hydrolysis under sterile conditions or in the presence of an undesirable preservative, such as sodium azide. The enzyme preparations from *Trichoderma harzianum* and *Trichoderma reesei* suffer from lack of thermostability which has resulted in lower hydrolysis efficiencies, high enzyme requirements and increased cost in carrying out hydrolysis under aseptic conditions. It is anticipated that the use of thermostable xylanases in effecting the enzymatic hydrolysis at elevated temperatures over long periods of time would enhance the technical and economic feasability of the hydrolysis process.

Xylanase production has been reported for many microorganisms including both fungi and bacteria. Most notable examples of this group of xylanase producers are *Trichoderma reesei* which most researchers world wide consider as a source of standard enzyme and *Trichoderma harzianum* strain E58 from the Forintek Canada Corp. culture collection. Although both fungi are prolific producers of extracellular xylanases, fungal growth and enzyme production can only be carried out at mesophilic temperature (28° C.). Consequently the fermentation requires considerable cooling water during fungal growth and is easily subjected to bacterial contamination. The xylanase enzymes produced are also thermally unstable, losing over 90% of their activities within half an hour incubation at 50° C. As a result, enzymatic hydrolysis of hemicellulose (xylan) using these enzymes has to be carried out at a lower temperature about 37° C. to 45° C. This in turn lowers the hydrolysis efficiencies, necessitates aseptic conditions during hydrolysis, as well as preventing prolonged enzyme use without replacement.

An object of the present invention therefore is to provide a process for producing thermally stable cellulolytic and xylanolytic enzymes, particularly xylanase and cellulase enzymes which would be useful in the above hydrolysis process. The further object of the present invention is to provide a hemicellulolytic microorganism which if cultured in a nutrient culture medium in a similar manner to the conventional hemicellulolytic microorganism to produce xylanase and cellulase, will produce thermally stable xylanase and cellulase enzymes.

It has now been found that fungus *Thermoascus aurantiacus*, particularly the strain *Thermoascus aurantiacus* 235E which is obtainable from the Forintek Culture Collection, Forintek Canada Corp. Ottawa, and which is also available from the American Type Culture Collection under the ATCC Accession Number 20882 Ontario is highly suitable for producing such thermally stable cellulolytic and xylanolytic enzymes, particularly thermally stable cellulase and xylanase.

According to the present invention therefore there is provided in a process for the production of cellulolytic and xylanolytic enzymes which comprises culturing a hemicellulolytic microorganism in a nutrient culture medium containing at least one of a cellulose or hemicellulose substrate, the improvement wherein the microorganism is *Thermoascus aurantiacus*, particularly strain 235E, to thus produce thermostable cellulolytic and xylanolytic enzymes.

The present invention also provides a biologically pure strain of the fungus *Thermoascus aurantiacus* 235E (C436), deposited in the Forintek culture collection, which is capable on culturing in a nutrient medium containing cellulosic and hemicellulosic substrate of producing thermally stable xylanase and cellulase enzymes.

Thus, in accordance with the present invention, the fungus *Thermoascus aurantiacus*, particularly strain 235E from the Forintek culture collection, is grown in a culture medium solution containing cellulosic and/or hemicellulosic substrates such as Solka Floc, oat spelt xylan, steamtreated aspenwood and sawdust, at a temperature at 45° C. or above under culturing conditions. Suitable culture media includes Vogel's medium and Mandel's medium. Xylanase activities are at their maximum levels in the culture medium after about 5 to 12 days whence the culture is filtered or centrifuged to obtain a culture filtrate. The culture filtrate containing the thermostable xylanase enzyme may be used directly for the hydrolysis of hemicellulose substrates at elevated temperatures of 50° C. or above for a prolonged period of time to produce pentose (xylose) sugars. For uses requiring the hydrolysis of a mixture of hemicellulosic and cellulosic substrates the culture filtrate containing both the thermostable xylanase and cellulase enzymes may be used directly to carry out such hydrolysis at elevated temperatures of 50° C. or above for prolonged periods of time to produce a mixture of pentose and hexose sugars.

In a particular embodiment of the present invention, the thermostable xylanase and cellulase enzymes in the culture filtrate may be concentrated either by rotary evaporation or by ultrafiltration. Thus, in particular the culture filtrate may be subjected to ultrafiltration through an ultrafiltration membrane having a low molecular weight cut-off point suitably between 1,000 and 20,000 daltons to obtain a xylanase and a cellulase rich retentate. Suitably the membrane has a low molecular weight cut-off point between 5,000 and 20,000, preferably between 5,000 and 15,000, more preferably between 5,000 and 12,000 and more desirably between 5,000 and 10,000. Suitably the membrane is a non-cellulosic membrane such as a polysulfone membrane. The retentate containing the concentrated thermostable xylanases and cellulases may be used for the hydrolysis of hemicellulosic or combined hemicellulosic and cellulosic substrates at elevated temperature of 50° C. or above for prolonged periods of time to produce a mixture of pentose and hexose sugars for subsequent fermentation or derivatization. Further, to obtain pure thermostable xylanase the crude fungal filtrate or the retentate from the ultrafiltration may be incubated at elevated temperature of at least 60° C. to selectively inactivate the cellulase activities in the mixture. Such pure thermostable xylanase can be used to selectively remove hemicellulose from mixed cellulose and hemicellulose substrates such as pulp.

The use of thermostable xylanase and cellulase enzymes obtained according to the present invention from *Thermoascus aurantiacus* 235E significantly enhances the technical and economic feasability of the hydrolysis set forth above. Being stable at higher temperatures of 50° to 70° C. the enzymes can be used at high reaction temperatures of 50° C. or above. This is highly desirable in that the rate of hydrolysis is increased drastically while the risk of contamination during hydrolysis is significantly reduced and is likely to be eliminated. Moreover the stability of the enzymes for prolonged periods of time at elevated temperatures enables the use of the enzymes for extended duration without replacement. This is also a very desirable property for enzymes to be used in commercial processes involving either enzyme recycling or a substrate fed batch process in continuous or semi-continuous hydrolysis systems. The ability to re-use the enzymes for prolonged periods of time also results in substantial reduction in the amount of enzymes required for the hydrolysis step thereby decreasing the cost of the enzyme production. Thus, the thermostable cellulases and xylanases produced in the process of the present invention have a substantial impact on the economic viability of the overall bioconversion process for wood residue utilization.

The use of a cellulase free xylanase enzyme preparation to selectively remove hemicellulose from pulp in manufacturing high quality cellulose such as rayon has already been effected as disclosed in our co-pending U.S. patent application Ser. No. 856934 filed Apr. 25, 1986, now U.S. Pat. No. 4,725,544, using the fungus *Trichoderma harzianum* E58 to produce the culture filtrate. The thermostable xylanase produced in the process of the present invention is also highly suitable in that the xylanase as present in the crude culture filtrates from the culturing of *Thermoascus aurantiacus* 235E is only contaminated by low cellulase activities (xylanase to carboxymethyl cellulase activity ratio around 75 to 1). The preparation may be considered to be essentially free from cellulase activity based on the relative thermostability of xylanase and cellulase activities. The xylanase activity of the xylanase produced by the process of the present invention is stable at 60° C. with a half-life of 4 days whereas the corresponding half-life of the cellulase is 8 hours. Thus the cellulase activity of the enzyme preparation may be reduced to negligible levels while maintaining the xylanase activity and the thermostable cellulase free xylanase enzyme may then be used in cleaning up cellulose pulp for industrial application.

In the process of the present invention the fungus *Thermoascus aurantiacus*, particularly strain 235E, is grown at elevated temperature, 45° C. or above and may be grown on a range of inexpensive commercial cellulosic substrates including steam exploded wood with or without fractionation and sawdust without treatment. The fungus so grown produces a full spectrum of other cellulolytic and xylanolytic enzymes and consequently the culture filtrates can serve as a source for both xylanase and cellulase enzymes for subsequent application. Initial characterization of the xylanase enzymes in the crude filtrate demonstrate that the enzyme activities are optimal at 75° C., with a half-life at 70° C. and 60° C. of 90 minutes and 4 days, respectively. Less than a 10% loss of enzyme activities occur when the enzymes are incubated at 50° C. for 12 weeks. The cellulase activities present in the same culture filtrates are also thermostable but to a much lower extent when compared with the xylanase activity. This property enables selective inactivation of the cellulase activities in favour of xylanase activities by simply incubating the enzyme preparations at elevated temperatures. Thus, for example, thermostability of xylanase and carboxymethyl cellulase activities at 60° C. differs by a factor of 12 (half-life of xylanase and cellulase at 4 days and 8 hours, respectively). This coupled with the initial prolific production of xylanase relative to cellulase at over a 75 to 1 ratio results in an essentially cellulase free thermostable xylanase for specific hydrolysis of hemicellulose (xylan). The thermostable xylanase enzyme or mixture of xylanase and cellulase enzyme may be used for the hydrolysis of biomass hemicellulose or combined hemicellulose and cellulose substrates, respectively. Both the xylanase and cellulase enzymes in the culture filtrates can be used directly or can be concentrated prior to applications as aforesaid by ultrafiltration through a membrane suitably with a molecular weight cut-off point at 10,000 daltons. Being thermostable, the xylanases or mixture of xylanases and cellulases in the same fraction can be used for the hydrolysis of hemicellulosic or combined hemicellulosic and cellulosic substrates at elevated temperature, 50° C. or above, for prolonged duration. The component pentose and hexose sugars obtained from the hydrolysis of the hemicellulose or mixed hemicellulose and cellulose can then be used for the subsequent fermentation and derivatization to produce a variety of fuels and chemicals.

*Thermoascus aurantiacus* strain 235E may be cultured at elevated temperatures of 45° C. or above to reduce the risk of contamination and the cooling water requirement during fermentation. Enzyme production by *Thermoascus aurantiacus* 235E however, is superior to other fungi or bacteria in several important regards, namely 1. The organism is an extremely prolific producer of xylanase enzymes up to 576 IU of xylanase activities per ml of original culture filtrate. 2. The same culture filtrates also exhibit a full spectrum of other cellulolytic and xylanolytic enzymes, including exoglucanases, endoglucanases, $\beta$-glucosidases, and $\beta$-xylosidases; and 3. Inexpensive biomass residues, such as sawdust without treatment or steam-exploded wood, can be used as the sole substrate for enzyme production. The extracellular nature of the enzyme also facilitates and drastically reduces the cost of enzyme harvesting in large scale commercial production schemes. In addition to the above benefits the xylanase enzymes also possess properties desirable in the actual hydrolysis of hemicelluloses. The enzymes in crude filtrates operated at an optimum temperature of 75° C. and are stable at elevated temperatures (half-life at 70° C. and 60° C. at 90 minutes and 4 days respectively). There is also no significant loss of xylanase activities at 50° C. after 12 weeks of incubation. It is therefore feasible to carry out enzymatic hydrolysis at 50° C. or above temperatures at which the enzymes have high efficiencies of catalysis. The enzymes can also last longer during use conditions without replacement, an ideal quality for enzyme recycling or substrate fed-batch in continuous hydrolysis processes. The use of higher temperatures for hydrolysis also eliminates or significantly reduces the risk of contamination during hydrolysis for extended periods in the absence of undesirable preservatives.

The thermostable xylanases present in the culture filtrate or concentrated in the retentates of the ultrafiltration process can be used to efficiently hydrolyse hemicellulosic substrates to fermentable sugars, predominantly pentoses. These thermostable cellulases present in the corresponding fractions can be used for the hydrolysis of cellulosic substrates to produce predominately glucose sugars for subsequent fermentation. The culture filtrates or their ultrafiltration retentates containing both xylanase and cellulase activities may also be used for the direct hydrolysis of pretreated biomass residues containing both cellulose and hemicellulose substrates to produce a mixture of fermentable hexose and pentose sugars. Alternatively the thermostable xylanases and cellulases in the retentates can be used in combined hydrolysis and fermentation of hemicellulose, cellulose or mixed cellulose and hemicellulose with a direct production of various fuels and chemicals. The pure thermostable xylanases may be used for the selective removal of contaminating hemicellulose (xylan) for high grade cellulose pulp for manufacturing rayon and cellophane and for reducing the amount of hemicellulose in aspen mechanical pulp. The crude thermostable xylanases may also be used in the bioconversion process during the hydrolysis of hemicelluloses derived from wood or agricultural residues to produce pentose (xylose) sugars, for subsequent fermentation to fuels and chemicals such as ethanol, acetone, butanol and butanediol and for the derivatization to form xylitol, artifical sweetners, furfural, etc. The thermostable xylanases can be used in processes for the manufacture of liquid coffee, the adjustment of wine characteristics, for the enhancement of astaxanthin extraction or the clarification of fruit juices and for the treatment of waste water from the wheat starch industry. The thermostable cellulases may be used for improved hydrolysis of the cellulose components of wood and agriculture residues to produce a glucose syrup which can then be converted to liquid fuels and chemical feed-stock. The cellulases may also be used in the manufacture of liquid coffee, clarification of fruit juices, treatment of waste water and from the wheat starch industry and enhancing the recovery in the distillation step in the alcoholic beverage industry. Since a mixture of xylanases and cellulases are generally required in several of the aforesaid applications it, is advantageous that the culture filtrates or the retentate fractions produced by the process of the present invention contained both active and thermostable xylanases and cellulases. Consequently the fractions may be used as the sole enzyme source for the hydrolysis of mixed cellulose and hemicellulose substrates as well as for manufacturing coffee, clarification fruit juices and treatment of waste water from food industry.

The present invention will be further illustrated by way of the following Examples:

EXAMPLE 1

PRODUCTION OF CELLULOLYTIC AND XYLANOLYTIC ENZYMES

A.

1. Organism, media, and culture conditions:

The thermophilic fungus, *T. aurantiacus* strain 235E from Forintek culture collection, was maintained on malt agar (MA) medium (Table 1) at 25° C. The stock cultures were then used to inoculate fresh malt agar slants and incubated at 45° C. in moisture-controlled incubator for 6-9 days until maximal mycelial growth was obtained. The slants were then maintained at 20° C. A spore inoculum was used to initiate growth in Erlenmeyer flasks (150 mL medium in 500 mL flasks) using various substrates at 1% (w/v) in either Vogel's medium (Table 2) or modified Mandel's medium (Table 3). The flasks were incubated at 45° C. on a shaking platform (100 rpm) for 7-10 days until maximal xylanase activities were obtained. The cultures were filtered through a Whatman glass fiber filter and the filtrates were used for enzyme assays and characterization studies.

2. Enzyme profile:

A full range of cellulolytic and xylanolytic enzyme activities were detected in the crude fungal culture filtrates (Table 4). Highest xylanase activities obtained from hemicellulose (oatspelt xylan) and cellulose (Solka Floc) were 575.9 IU/mL and 365.8 IU/mL, respectively. The water-insoluble residues of steam-exploded aspenwood (240° C., 80s), which contained predominantly cellulose and lignin, as well as sawdust (with or without ball-milling) also demonstrated promise as potential inexpensive realistic substrates for future large scale commercial production of the xylanase enzymes.

INITIAL CHARACTERIZATION OF XYLANASE ENZYMES

B.

crude culture filtrates without further treatment were used instead of purified enzyme 1. Optimal xylanase activity was observed at pH 4.8-5.8 and 70°-80° C.

2. Xylanase activity was thermostable with half-life (i.e., the time of incubation at a particular temperature during which 50% of the original enzyme activity is lost) at 70° C. and 60° C. being around 1½ h and 4 d, respectively. Xylanase activity was stable at 50° C. for at least 12 weeks.

3. The crude culture filtrate could hydrolyze oatspelt xylan at 70° C., 60° C., and 50° C. to release mixtures of xylotetraose, xylotriose, xylobiose (predominant product), xylose, and arabinose (Table 5).

C. APPLICATIONS OF THERMOSTABLE XYLANASE ENZYMES

1. Hydrolysis of hemicellulose by xylanase in fungal culture filtrate: Xylanase in culture filtrate can be used directly, or after being concentrated either by rotary evaporation or by ultrafiltration, for the effective hydrolysis of xylan (model hemicellulose substrate) or of aspenwood hemicellulose present in the water-extract of steam-exploded wood (a realistic substrate obtained as a major byproduct in bioconversion processes to produce fuels and chemicals from wood or agricultural residues) (Table 6). Based on the hemicellulose (xylan) content of the substrate, hydrolysis of hemicelluloses by the enzyme preparations can approach near completion within 48 hours, even at high substrate concentrations (10%, dry weight/vol).

2. Combined hydrolysis and fermentation of hemicelluloses for the direct production of fuels and chemicals: Xylanase enzyme preparations from 1 can be used in conjunction with fermentative organisms to simultaneously hydrolyze hemicellulose to sugars and ferment the sugars released to a variety of fuels and chemicals. An example of this is the use of *Klebisella pneumoniae* (*Klebsiella oxytoca* ATCC 8724) with the enzyme preparation to produce 2,3-butanediol, ethanol, acetoin, and acetic acid from xylan and steamexploded aspenwood hemicellulose (Table 7).

3. Hydrolysis of mixed cellulose and hemicellulose substrates by mixed xylanase and cellulase enzyme preparations: The thermostable xylanase enzyme preparations obtained from 1/ also contains thermostable cellulases and can therefore be used for the hydrolysis of substrates containing both cellulose and hemicellulose carbohydrates. For an example, steam-exploded aspenwood containing around 54.0% (w/w) cellulose (hexosan) and 13.4% (w/w) hemicellulose (pentosan) can be efficiently hydrolyzed to release a mixture of hexose and pentose sugar (Table 8).

4. Combined hydrolysis and fermentation of mixed cellulose and hemicellulose substrates by mixed xylanase and cellulase enzyme preparations in conjunction with fermentative microorganisms: Butanendiol and ethanol production can be achieved by incubating the thermostable enzyme preparations obtained from 1/ and *K. pneumoniae* with steam-exploded aspenwood.

5. Selective hydrolysis of hemicellulose in substrates containing both cellulose and hemicellulose by cellulase-free xylanase enzyme preparations: Based on the differential thermostability of the xylanase and cellulase enzymes present in culture filtrates, enzyme preparations enriched with xylanase activities with negligible level of cellulase activities can be obtained. For an example, half-life of xylanase activities at 60° C. is 4 days while that of cellulase (carboxymethylcellulase) activities is only 8 h. This twelve fold difference in thermostability, together with the initial xylanase activities in the culture filtrates being over 75 fold higher than the cellulase activities, could result in a simple yet novel method for obtaining essentially cellulase-free thermostable xylanase enzyme preparations. Such thermostable pure xylanase enzyme can be of great commercial potential, e.g., in selectively cleaning up contaminating amount of hemicellulose present in commercial cellulose pulp for the manufacture of high grade cellulose (such as rayon or cellophane).

TABLE 1

| Composition of malt agar (MA) medium | |
|---|---|
| Difco Bacto Malt extract | 20.0 g/L |
| Difco Bacto agar | 20.0 g/L |
| Distilled water | 1000 mL |

TABLE 2

| Compostion of Vogel's Medium | |
|---|---|
| Medium Ingredients | Concentration (/L) |
| Salts: | |
| $Na_3$ Citrate.$2H_2O$ | 2.5 g |
| $KH_2PO_4$ | 5.0 g |
| $NH_4NO_3$ | 2.0 g |
| $MgSO_4.7H_2O$ | 0.2 g |
| $CaCl_2.2H_2O$ | 0.1 g |
| Vitamins: | |
| Biotin | 0.5 μg |
| Myoinositol | 2.0 mg |
| Ca-panthothenate | 0.2 mg |
| Pyridoxine - HCl | 0.2 mg |
| Thymine - HCl | 0.2 mg |
| Trace Elements: | |
| Citric Acid.$H_2O$ | 5.0 mg |
| $ZnSO_4.7H_2O$ | 5.0 mg |
| $Fe(NH_4)_2(SO_4)_2.5H_2O$ | 1.0 mg |
| $CuSO_4.5H_2O$ | 0.25 mg |
| $MnSO_4.2H_2O$ | 0.05 mg |
| $H_3BO_3$ | 0.05 mg |
| $Na_2Mo_2O_4.2H_2O$ | 0.05 mg |
| Bacto-Peptone | 1.0 g |
| Tween 80 | 2.0 mL |
| Carbon source | 10.0 g |

TABLE 3

| Composition of Mandel's Medium | |
|---|---|
| Medium Ingredients | Concentration (/L) |
| Salts: | |
| $(NH_4)_2.SO_4$ | 1.4 g |
| $KH_2PO_4$ | 2.0 g |
| $MgSO_4.7H_2O$ | 0.15 g |
| Trace Elements: | |
| $FeSO_4.7H_2O$ | 5.0 mg |
| $MnSO_4.H_2O$ | 1.6 mg |
| $ZnSO_4.7H_2O$ | 1.4 mg |
| $CoCl_2$ | 2.0 mg |
| $CaCl_2.2H_2O$ | 0.4 g |
| Urea | 0.3 g |
| Peptone | 1.0 g |
| Tween 80 | 0.2 g |
| Carbon source | 10.0 g |

TABLE 4

| Production of extracellular cellulolytic and xylanolytic enzymes by *T. aurantiacus* strain 235E | | | | |
|---|---|---|---|---|
| | Enzyme activities (IU/mL) | | | |
| Substrate (1%, w/v) | Xylanase | Endo-glucanase | Filter paper | B-gluco-sidase |
| A. Volgel's medium | | | | |
| Solka Floc | 365.8 (7) | 10.1 (7) | 0.16 (5) | 0.74 (10) |
| SEA-WI | 98.2 (10) | 2.9 (10) | 0.16 (10) | 0.31 (10) |
| Sawdust | 40.5 (10) | 0.6 (10) | 0.05 (4) | 0.14 (10) |
| Sawdust (Ball-milled) | 174.4 (10) | 5.6 (7) | 0.27 (10) | 1.34 (10) |
| Xylan | 575.9 (10) | 7.3 (10) | 0.40 (10) | 0.66 (10) |
| SEA | 66.1 (10) | | | |
| SEA-WS | 6.2 (10) | | | |
| B. Modified Mandel's medium | | | | |
| Solka Floc | 94.6 (10) | 7.3 (10) | 0.13 (4) | 0.39 (10) |
| SEA-WI | 62.6 (7) | 2.7 (10) | 0.09 (10) | 0.18 (10) |
| Sawdust | 61.6 (10) | 0.9 (10) | 0.05 (4) | 0.16 (10) |

TABLE 4-continued

Production of extracellular cellulolytic and
xylanolytic enzymes by *T. aurantiacus* strain 235E

| Substrate (1%, w/v) | Enzyme activities (IU/mL) | | | |
|---|---|---|---|---|
| | Xylanase | Endo-glucanase | Filter paper | B-gluco-sidase |
| Sawdust (Ball-milled) | 80.7 (10) | | | |
| Xylan | 283.3 (10) | | | |
| SEA | 39.1 (10) | | | |
| SEA-WS | 3.0 (10) | | | |

Notes:
1/ Values in parenthesis were the respective incubation time when maximum activities of the enzyme were detected in the culture filtrates
2/ B-xylosidase activity was also assayed in cultures grown on solka floc or xylan in Vogel's medium to be around 0.07 IU/mL
3/ Extracellular protein concentrations in filtrates of cultures grown on Solka Floc or xylan in Vogel's medium were 0.26 mg/mL and 0.90 mg/mL, respectively.

TABLE 5

Hydrolysis of xylan by culture filtrates of *T. aurantiacus* 235E at various temperatures.

| Temp. (°C.) | Reducing sugars (g/L) | Sugars by HPLC (g/L) | | | | |
|---|---|---|---|---|---|---|
| | | Xylose | Xylobiose | Xylotriose | Xylotetraose | Arabine |
| 70 | 24.8 | 4.8 | 11.5 | 6.2 | 9.2 | 1.2 |
| 60 | 22.0 | 4.5 | 10.4 | 5.0 | 8.8 | 0.9 |
| 50 | 18.5 | 1.6 | 6.0 | 4.4 | 7.2 | 0.0 |

Hydrolysis was carried out on oat-spelt xylan (5%, w/v) using crude culture filtrate of *T. aurantiacus* 235E (at xylanase activity of 70 IU/mL). Incubation was carried out at various temperatures with shaking for 24 h.

TABLE 6

Hydrolysis of Hemicellulose Substrates by culture filtrates of *T. aurantiacus* 235E concentrated by ultrafiltration.

| Substrate a Conc. | R.S. (g/L) | Sugars by HPLC (g/L) | | | | |
|---|---|---|---|---|---|---|
| | | Xylose | Xylobiose | Xylotriose | Xylotetraose | Arabinos |
| Xylan: | | | | | | |
| 20 g/L | 8.7 | 4.7 | 6.7 | 0.0 | 0.5 | 1.1 |
| 50 g/L | 24.1 | 12.7 | 12.2 | 0.3 | 0.0 | 2.4 |
| 100 g/L | 48.1 | 33.8 | 22.3 | 1.7 | 7.1 | 7.0 |
| Steam-Exploded Aspenwood Water-Solubles: | | | | | | |
| 20 g/L | 5.3 | 4.9 | 6.1 | 0.1 | 0.0 | 1.1 |
| 50 g/L | 10.2 | 11.2 | 14.3 | 0.9 | 0.0 | 3.6 |
| 100 g/L | 24.1 | 23.8 | 23.9 | 1.7 | 2.0 | 4.8 |

Hydrolysis was carried out at 50° C. with shaking for 48 h, using culture filtrates of *T. aurantiacus* 235E concentrated by passage through a Pellicon membrane with molecular weight cut-off of 10 KD.

TABLE 7

Butanediol and ethanol production by a CHF approach, using *Klebsiella pneumoniae* and *T. aurantiacus* culture filtrate concentrated by ultrafiltration.

| Xylon (g/L) | Butanediol (g/L) | | | Ethanol (g/L) | | |
|---|---|---|---|---|---|---|
| | Day 1 | Day 2 | Day 4 | Day 1 | Day 2 | Day 4 |
| 20 | 1.3 | 1.6 | 2.0 | 0.3 | 0.4 | 0.5 |
| 50 | 2.4 | 5.2 | 5.0 | 0.6 | 1.9 | 1.8 |
| 100 | 3.7 | 9.2 | 12.2 | 1.0 | 3.2 | 4.0 |

TABLE 8

Enzymatic hydrolysis of combined cellulose and hemicellulose substrates by the thermostable enzyme preparations from *T. aurantiacus*

| SEA conc. (g/L) | Reducing sugars released (g/L) | % Hydrolysis (based on carbohydrate content of substrate) |
|---|---|---|
| 20 | 7.4 | 56.5 |
| 50 | 16.8 | 51.8 |

Hydrolysis was carried out at 50° C. for 48 hours using culture filtrates of *T. aurantiacus* concentrated by ultrafiltration. Substrate used was aspenwood after steam-explosion (240° C., 80s: without extraction).

EXAMPLE 2

In the accompanying drawings of Example 2:

FIG. 1: Xylanase production by *T. aurantiacus* 235E grown on various hemicellulosic and lignocellulosic substrates. ✦, oat-spelt xylan; ●, steam-exploded aspenwood; and ▲, the water-soluble fraction (hemicellulose) of steam-exploded aspenwood.

Figure 2:
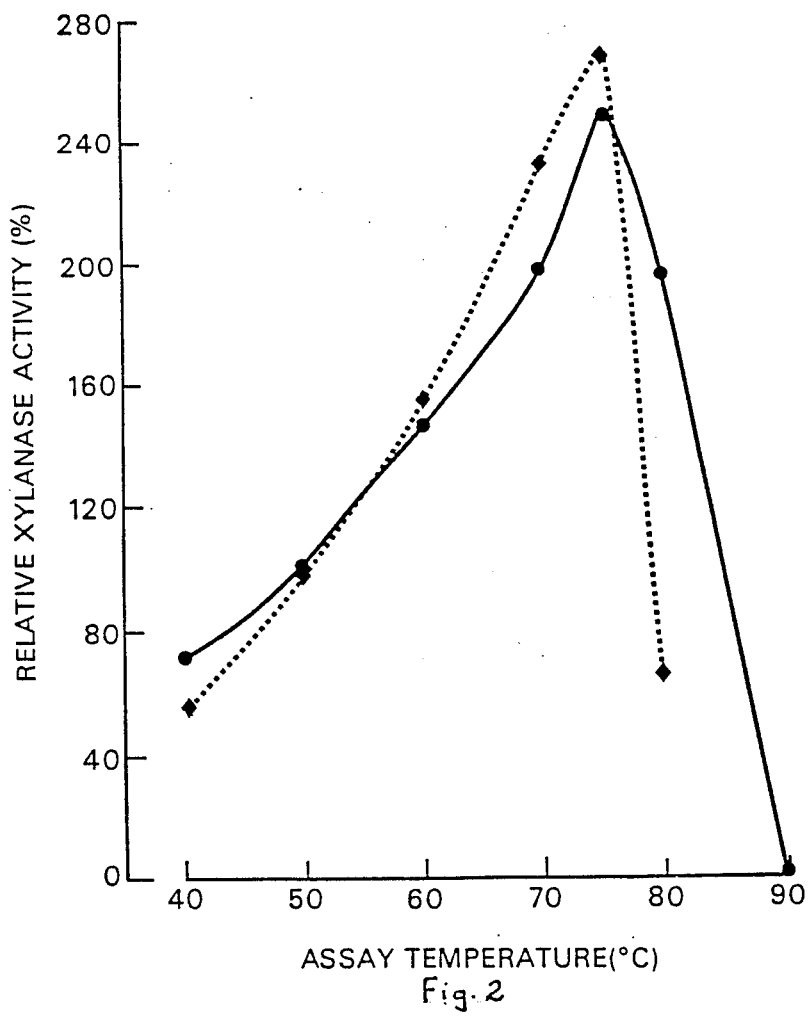

FIG. 2: Temperature optimum of xylanase and B-xylosidase activities assayed in citrate-phosphate buffer (pH 5.0) for 30 min. Activities obtained at 50° C. were taken as the 100% reference levels for both enzymes. ●, xylanase activity; ◆, B-xylosidase activity.

Figure 3:
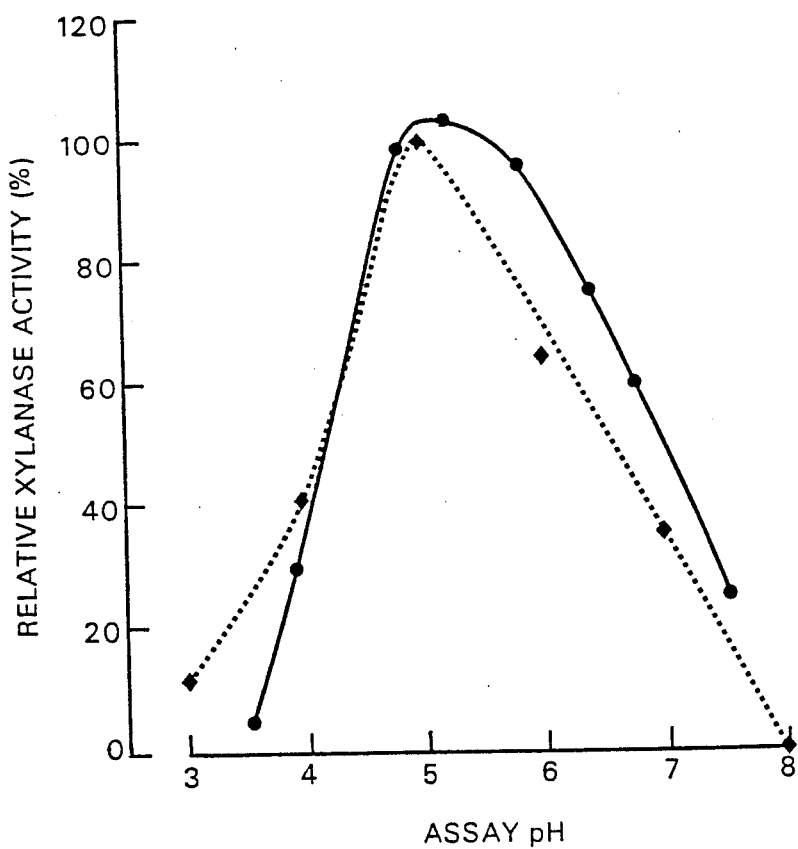

FIG. 3: pH optimum of xylanase and B-xylosidase activities assayed in citrate-phosphate buffer at 50° C. for 30 min. Activities obtained at pH 4.8 and 5.0 were taken as the 100% reference levels for xylanase and B-xylosidase, respectively. ●, xylanase activity; ✦, B-xylosidase activity.

Figure 4:
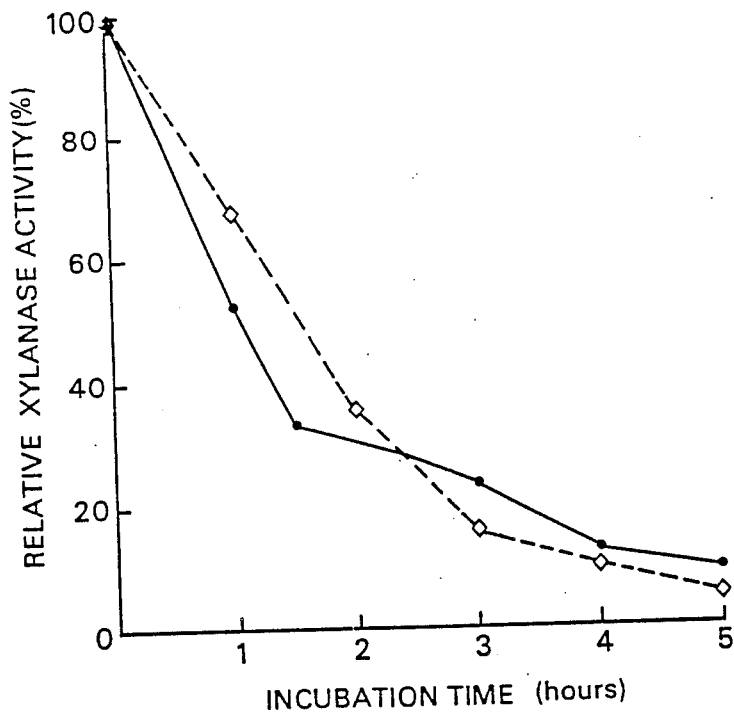

FIG. 4: Thermostability of xylanase activity at 70° C. ●, filtrate of fungal culture grown on solka floc; ◇, filtrate of fungal culture grown on xylan.

Figure 5:
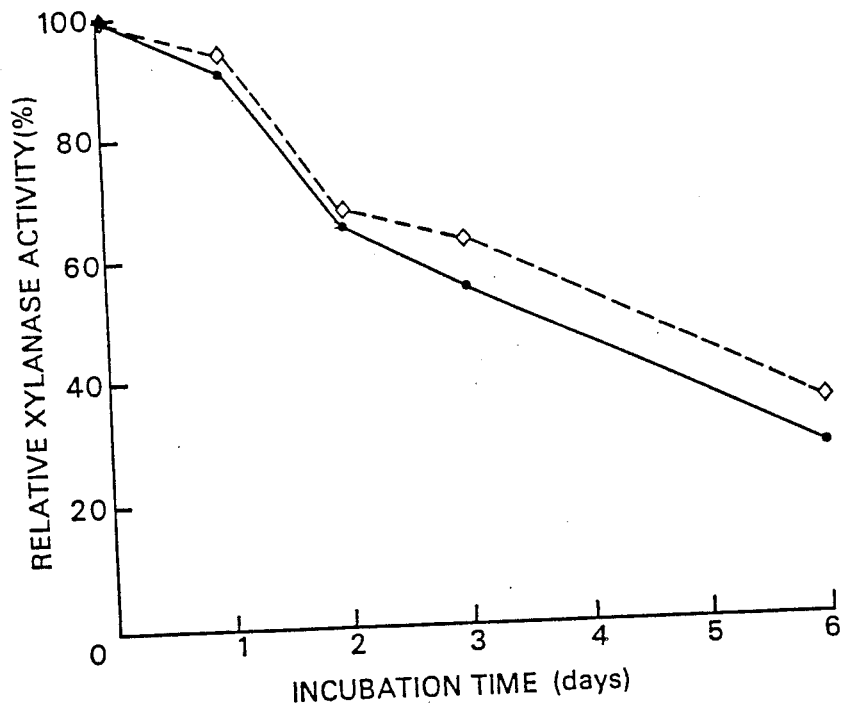

FIG. 5: Thermostability of xylanase activity at 60° C. ●, filtrate of fungal culture grown on solka floc; ◇, filtrate of fungal culture grown on xylan.

MATERIALS AND METHODS

Microorganisms

All of the thermophilic fungi used were taken from the Forintek culture collection (Table 9). Cultures were generally maintained on malt agar (MA) medium, containing 20 g of Difco Bacto Malt extract and 20 g of Difco Bacto agar per liter of distilled water. However, strains B499 (unclassified), C416 (Mucor spp.), C433 (*Myricoccum albomyces*), C437 (*Malbranchea pulchella*), and C491 (*Thielavia terrestris*) were maintained on yeast phosphate soluble starch (UPSS) agar medium, containing 4.0 g of Difco Bacto yeast extract; 1.0 g of potassium monophosphate; 0.5 g of magnesium sulfate heptahydrate; 15.0 g of Difco soluble starch; and 20.0 g of Difco Bacto agar per liter of distilled water. Fungal cultures to be used as inocula were grown on their respective maintenance media at 45° C. for 6–9 days to maximize mycelial growth, and were then maintained at room temperature. A spore inoculum was then used to initiate growth in tubes and in shake flasks.

Media and culture conditions

Initial screening of cellulolytic and xylanolytic fungi was carried out on solid medium supplemented with gelrite and various cellulosic and hemicellulosic substrates as detailed in the following section. Incubation was carried out at 45° C. in moisture-saturated plastic bags to minimize desiccation due to the high incubation temperature. The tubes were analyzed weekly for the depth of clearing of the substrates.

Studies on the production of cellulase and xylanase enzymes in the culture filtrates were carried out in 150 ml of aqueous medium (in 500 ml Erlenmeyer flasks). Unless otherwise specified, all fungi were grown in Vogel's medium, Montenecourt, B. S. and Eveleigh, D. E. *Appl. Environ. Microbiol.* 1977, 34, 777–784 containing 1% (w/v) Solka Floc BW 300 (Brown and Co., N.H., U.S.A.) as the cellulose substrate. The flasks were incubated at 45° C. on a shaking platform (100 rpm). Samplings were carried out at various times during the incubation period by aseptically withdrawing a portion of the fungal cultures. Cultures were then filtered through a Whatman glass fiber filter and the filtrates were assayed for the activities of the various hydrolytic enzymes.

Preliminary studies on maximizing the production of xylanase and cellulase enzymes by *Thermoascus aurantiacus* 235E were carried out in aqueous medium, using Vogel's or modified Mandel's medium, Mandel, M. *Bioconversion of Cellulose Material to Energy, Chemicals and Microbial Protein* (Ghose, T. K., ed.), ITT, New Delhi, India, 1977 on various cellulosic substrates as detailed in the following section. Incubation conditions and sampling procedures were carried out as earlier described. All studies were carried out in duplicate and repeated at least once.

Substrates

All substrates used in the tube-clearing assay, except acid swollen cellulose, were all ball-milled for 3 weeks prior to use to facilitate analysis of tube clearing. Unless otherwise specified, all substrates used in submerged aqueous medium were not ball-milled. Substrates used, other than the Solka Floc already mentioned, included:

(1) Aspenwood sawdust (ASD)

(2) Steam-exploded aspenwood (SEA). Aspenwood chips pretreated by steaming at 240° C. for 180 seconds in a Masonite-type reactor and then explosively decompressed, Saddler, J. N., Brownell, H. H., Clermont, L. P., and Levitin, N. *Biotechnol. Bioeng.* 1982, 24, 1389–1402.

(3) Steam-exploded aspenwood, water-insolubles (SEA-WI). Aspenwood chips treated as in (2) except that the resulting materials were further extracted with water at room temperature for 2 hours at a concentration of 5% (dry weight per volume).

(4) Steam-exploded aspenwood, water-solubles (SEA-WS). The water extracts obtained in (3) which were concentrated to dry powder by rotary evaporation under high vacuum.

(5) Aspenwood xylan prepared by alkali treatment of extractive-free aspenwood sawdust by the modified methods of Jones et al, Jones, J. K. N., Purves, C. B. and Timell, T. E. *Can. J. Chem.* 1961, 39, 1059–1066 and Koshijima et al, Koshijima, T., Timell, T. E. and Zimbo, M. *J. Polymer Sci.* 1965, 11, 265–270.

(6) Oat-spelt xylan purchased from Sigma Chem. Co. (St. Louis, Mo., U.S.A.)

(7) Acid swollen cellulose (ASC)

(8) Cellulose-Whatman No. 1 filter paper (CW1)

Analytical methods

Total reducing sugars were estimated colorimetrically using dinitrosalicylic acid reagent, Miller, G. L. *Anal Chem.* 1959, 31, 426–428.

Xylanase (Endo-1,4-$\beta$-D-xylanase) activity was determined by incubating 1 ml of an appropriately diluted enzyme preparation (crude fungal culture filtrate) with 10 mg of oat-spelt xylan in 1 ml of 0.1M citrate phosphate buffer (ph 5.0) at 50° C. for 30 minutes. The reaction was terminated by the addition of 3 ml of 3,5-dinitrosalicylic acid reagent. One unit of xylanase activity was defined as 1 $\mu$mole of xylose equivalents released per minute. Filter paper activity was determined by the method of Mandel et al (Mandel, M. Andreotti, R. and Roche, C., *Biotechnol Bioeng. Symp.* 6 1976, 21–34. Endogluconase (carboxymethycellulase) and $\beta$-glucosidase (salicinase) activities were assayed under conditions previously established, Saddler, J. N., Hogan, C. M., Chan, M. K. -H and Louis-Seize, G. *Can. J. Microbiol.* 1982, 28, 1311–1319. Xylobiase ($\beta$-xylosidase) activity was determined using p-nitrophenyl xylopyranoside reagent, Dekker, R. F. H. *Biotechnol. Bioeng.* 1983, 25, 1127–1146. Soluble protein was determined by the method of Lowry et al, Lowry, O. H., Rosebrough, N. J., Farr, A. L. and Randall, R. J. *J. Biol. Chem.* 1951, 193, 265–275 as modified by Tan et al, Tan, L. U. L., Chan, M. K. -H and Saddler, J. N. *Biotechnol. Lett.* 1984, 6, 199–204 using bovine serum albumin as standard.

Optimization of assay conditions

Studies on pH optimizations were performed in 0.05M citrate phosphate buffer adjusted to initial pH values of 3.5 to 7.5. The reaction mixtures, containing oat-spelt xylan (0.5%, w/v) and an appropriately diluted enzyme preparation (crude culture filtrate), were incubated at 50° C. for 30 min. Temperature optimization studies were similarly carried out in citrate phosphate buffer at pH 5.0 and assayed for reducing sugars released after incubation at various temperatures for 30 min.

Thermostability studies

Thermostability of the enzyme activities of the crude fungal culture filtrates were determined by incubating the filtrates at 70° C., 60° C., and 50° C. for various durations ranging from hours to weeks. The treated filtrates were then assayed for the respective enzyme activities by incubating an appropriately diluted aliquot of the treated sample with the assay substrate in citrate phosphate buffer at pH 5.0 and 50° C. for 30 min., as described in the previous section.

Chemicals

Solka Floc (B. W. 300 F.C.) was obtained from Brown and Co., Berlin, NH. Carboxymethylcellulose (medium viscosity, D.P. 1100), salicin, oat-spelt xylan, and p-nitrophenyl xylopyranoside were purchased from Sigma Chem. Co. (St. Louis, MO.). 3,5-Dinitrosalicylic acid was purchased from Eastman Kodak Co. (Rochester, NY). All other chemicals were obtained from Fisher Chem. Co. (Ottawa, Canada) and of reagent grade.

RESULTS AND DISCUSSION

Initially twenty-one thermophilic fungal strains in Forintek culture collection were screened for xylanase and cellulase enzyme production in solid medium using the tube-clearing method as proposed by Tansey. Based on the results obtained from earlier studies on xylanase and cellulase production by mesophilic fungi, aspenwood xylan was selected as the substrate in the present study for detecting the production and secretion of extracellular fungal xylanase enzymes, while acid swollen cellulose and aspenwood sawdust were chosed as substrates to screen for the cellulase enzymes. Whatman filter paper, and steam-exploded aspenwood cellulose (i.e., the water-insoluble fraction of steam-exploded aspenwood) were all found to be unsatisfactory as routine assay substrates since they generally did not result in clear zones of hydrolysis (data not shown).

Table 10 summarizes the results obtained from the solid medium tube clearing assay for both the xylanase and cellulase production by the thermophilic fungi. All fungal strains, with the possible exceptions of strains B499, C416 (Mucor sp.), and C491 (*Thielavia terrestris*), showed visible growth on all the substrates used. These three strains, as well as strain B519, also failed to exhibit any clearing on most or all of the substrates tested. Two other strains, *Phanerochaete chrysosporium* A387 and *Taloromyces emersonii* C463, also showed low overall clearing abilities on all the substrates used. All the remaining strains were found to be strongly active in clearing aspenwood xylan, with nine of the strains resulting in complete substrate clearing within 2–3 weeks. Only two strains, *Malbranchea pulchella* C437 amd *Humicola lanuginosa* C466, which showed good substrate clearing when grown on xylan, failed to exhibit any apparent clearing when grown on all cellulosic substrates. Substrate clearing by the thermophilic strains grown on aspenwood sawdust and acid-swollen cellulose generally showed good correlation, with most fungal strains exhibiting stronger clearing activities when grown on aspenwood sawdust. There were, however, several exceptions to this trend, particularly with one strain, *Myricoccum albomyces* C433, which showed complete clearing of acid swollen cellulose and yet poor clearing of aspenwood sawdust. Among all the thermophilic fungal strains, *Sporotrichum thermophile* C419, *Phanerochaete chrysosporium* A435, *Thermoascus aurantiacus* C412 and 235E appeared to be the best strains in the overall clearing of both the cellulosic and hemicellulosic substrates.

To ensure that the tube clearing assay is a true reflection of the abilities of the organisms to produce extracellular hydrolytic enzymes, the fungi were also grown in liquid cultures and analyzed for their enzyme production and secretion in culture filtrates (Table 11). General correlations between the tube assay for estimating the cellulolytic and xylanolytic potential of a particular fungal strain and the actual enzyme production in liquid cultures were obtained. Several strains which showed poor clearing in tubes, such as B499, C491 (*Thielavia terrestris*), and C416 (Mucor sp.) (Table 10), also exhibited low cellulase or xylanase enzyme activities in their culture filtrates (Table 11). Other strains, such as *Thermoascus aurantiacus* C412 and 235E. showed good clearing of the substrates in the tube assay (Table 10) and also good enzyme production in liquid medium (Table 11). There were, however, several notable exceptions to the general correlation of the tube assay and enzyme production in liquid medium. *Phanerochaete chrysosporium* A387, which showed no apparent clearing on xylan and little clearing on cellulosic substrates in solid medium (Table 10), was found to produce high levels of endoglucanase and xylanase activity when grown on Solka Floc in liquid medium (Table 11). On the other hand, *P. chrysosporium* A435, which demonstrated near complete clearing on all substrates when grown in solid medium (Table 10), was found to produce only very low levels of both cellulase and xylanase enzymes in liquid medium (Table 11). This, however, could be because the medium and culture conditions for the fungi used in the screening studies have not yet been established, thereby preventing optimal production of the desired enzymes. It is apparent, however, that both the tube clearing assay and the liquid culture studies are useful in screening work, and that the choice of one approach over the other will likely depend on the number of cultures to be studied.

*Thermoascus aurantiacus* 235E was demonstrated to be the best producer of extracellular xylanase in liquid culture (Table 11). Culture filtrates of the fungus were also found to exhibit high cellulase activities, with particularly high B-glucosidase activity. A preliminary study was therefore initiated to examine enzyme production by the fungus when grown in common fungal fermentation medium on various cellulosic substrates of commercial potential (such as steam-exploded aspenwood and aspenwood sawdust) (Table 12). In general, Vogel's medium appeared to be more favorable for fungal enzyme production than Mandel's medium (Tables 11 and 12). However, the potential of using the simpler and less expensive Mandel's medium in place of Vogel's medium was still demonstrated by the high levels of xylanase and cellulase activities detected in the filtrates of cultures grown in Mandel's medium. Solka Floc appeared to be the most effectivce substrate for enzyme production, but high levels of extracellular xylanase (with accompanying cellulase) activities were also detected in filtrates of cultures grown on steam-exploded aspenwood cellulose (i.e., water-insoluble residues of steam-exploded aspenwood) and sawdust without any treatment. The economic potential of using these latter substrates should be further explored, particularly with respect to sawdust. Being inexpensive and abundant, they should be more attractive substrates for large scale enzyme production. The present study also showed that sawdust after ball-milling became an excellent substrate for xylanase and cellulase enzyme production (Table 12). The levels of filter paper activity and B-glucosidase activity in filtrates of cultures grown on ball-milled sawdust actually surpassed those obtained with Solka Floc (Tables 11 and 12). Although it is unlikely that ball-milling would be a realistic pretreatment method due to its high energy cost, it is conceivable that other pretreatment methods could be tested to more fully exploit sawdust as a substrate for enzyme production. The present level of 61.6 IU/ml of xylanase activity produced from completely untreated sawdust might already constitute an economical method of enzyme production. The decision on whether to pretreat sawdust to enhance enzyme production might rest on the compromise of enzyme yields versus the additional pretreatment costs.

The production of extracellular xylanase(s) from hemicellulose-containing substrates was also studied (FIG. 1). Vogel's medium was again shown to be superior to Mandel's medium for enzyme production. A xylanase activity of 66.1 IU/ml was obtained in filtrates of cultures grown in Vogel's medium on unextracted steam-exploded aspenwood, demonstrating that the crude lignocellulosic residue could serve as an effective substrate for enzyme production as well. The hemicellulose-rich water-soluble fractions of steam-exploded aspenwood, on the other hand, resulted in poor fungal growth and enzyme production. Similar findings had earlier been reported with enzyme production from Trichoderma species and was attributed to the presence of water-soluble inhibitors associated with the fraction, Saddler, J. N. and Mes-Hartree, M. *Biotechnol. Adv.* 1984, 2, 161–181. Oat-spelt xylan was found to be the best substrate for xylanase production. Up to 575.9 IU/ml of xylanase activity was detected in the filtrates of cultures grown in xylan in Vogel's medium (FIG. 1), surpassing the xylanase production in cultures grown on Solka Floc (Table 11, for strain 235E). Maximum enzyme production occurred at day 10, after which the enzyme activities in the culture filtrates started to decline (data not shown). At the time when maximum xylanase activity was detected in the culture filtrate, the corresponding β-xylosidase, endoglucanase, filter paper, β-glucosidase, and protein levels in the filtrates were 1.63 IU/ml, 8.70 IU/ml, 0.30 IU/ml, 0.87 IU/ml, and 1.33 mg/ml, respectively. To our knowledge, the level of xylanase activity (both in terms of IU/ml and IU/mg, using standard assay techniques) detected in the crude culture filtrates of *T. aurantiacus* surpassed all other microbial systems reported in the literature. Moreover, being thermophilic, the fungus could be grown at elevated temperature (45° C. or above) which should reduce the risk of microbial contamination and the cooling requirements for the fermentation process.

Preliminary characterization of the xylanase activity in the crude culture filtrate of *T. aurantiacus* was then carried out. Both the xylanase and β-xylosidase activities in the filtrates exhibited temperature optima at 75° C. (FIG. 2) and pH optima around 5.0 (FIG. 3). The xylanase activity in the crude filtrate was also demonstrated to be thermally stable. The half-lives of the enzyme at 70° C. and 60° C. were around 1.5 hours and 4 days, respectively (FIGS. 4 and 5). The patterns were essentially similar to xylanase activity in filtrates of cultures grown on a cellulosic substrate (Solka Floc) or on a hemicellulosic substrate (oat-spelt xylan). The half-life of the enzymes at 50° C. have not yet been determined, since over 90% of the activity remained in the filtrates after incubation at 50° C. for 12 weeks. The corresponding β-xylosidase activity also appeared to be thermostable, though not to the same extent as the xylanase activity (half-life at 70° C. and 60° C. at around 36 minutes and 2.4 hours, respectively).

The observed thermostability of the xylanase in the crude culture filtrates of *T. aurantiacus* was unusual when compared to the xylanases reported in the literature. Although detailed information on the thermostability of the reported xylanases was generally lacking, xylanases produced by a wide range of mesophilic fungi and bacteria usually showed optimal enzyme activity at around 50° C. Woodward, J. *Topics in Enzyme and Fermentation Biotechnology* 1984, 8 9–30; Dekker, R. F. H. and Richards, G. N. *Adv. Carbohyd. Chem Biochem.*, 1976, 32, 277–352). Recent interest in thermostable enzymes have led to discovery of several thermophilic or thermotolerant fungi and bacteria capable of producing thermostable xylanases. These include *Malbranchea pulchella*, an alkalophilic thermophilic Bacillus, *Thermomonospora sp., Clostridium stercorarium, Saccharomonospora viridis, Thermomonospora fusca, T. curvata, T. chromogena, Melanocarpus albomyces, Thielavia terrestris, Sporotrichum thermophile, Talaromyces byssochlamydoides*, and *Ceratocystis paradoxa*. Direct comparisons of enzyme activities and thermostability among various organisms were not always possible due to variations in the methodologies used. Nevertheless, based on published reports, it would appear that the xylanases of *T. aurantiacus* were among the most thermostable xylanases produced. This finding, in combination with the exceedingly high levels of xylanase activities obtained in crude culture filtrates, strongly indicate the potential of the enzyme in future commercial applications.

CONCLUSIONS

Screening of thermophilic cellulolytic and xylanolytic fungi in Forintek's culture collection successfully identified *T. aurantiacus* 235E as an extremely prolific producer of extracellular xylanase enzymes. The same culture filtrate also exhibited a full spectrum of other cellulolytic and xylanolytic enzyme activities. Enzyme production could be achieved at elevated temperatures even in cultures grown on inexpensive biomass residues, such as untreated sawdust and steam-exploded aspenwood. The xylanase enzyme demonstrated unusually high thermostability and could have potential in future large scale biomass hydrolysis or combined hydrolysis and fermentation processes.

TABLE 9

| Strain | Fungus | Classification |
|---|---|---|
| A387 | *Phanerochaete chrysosporium* | Basidiomycete |
| A435 | *Phanerochaete chrysosporium* | Basidiomycete |
| B499 | Unclassified | Unclassified |
| B508 | Unclassified | Unclassified |
| B519 | Unclassified | Unclassified |
| C341 | Unclassified | Unclassified |
| C372 | *Sporotrichum thermophile* | Deuteromycete |
| C375 | Unclassified | Unclassified |
| C412 | *Thermoascus aurantiacus* | Ascomycete |
| C416 | Mucor sp. | Phycomycete |
| C419 | *Sporotrichum thermophile* | Deuteromycete |
| C424 | Unclassified | Unclassified |
| C433 | *Myricoccum albomyces* | Deuteromycete |

List of thermophilic fungi in Forintek culture collection studied.

TABLE 9-continued

List of thermophilic fungi in Forintek culture collection studied.

| Strain | Fungus | Classification |
|---|---|---|
| 235E | Thermoascus aurantiacus | Ascomycete |
| C437 | Malbranchea pulchella | Deuteromycete |
| C463 | Taloromyces emersonii | Deuteromycete |
| C464 | Thielavia terrestris | Ascomycete |
| C465 | Allescheria terrestris | Ascomycete |
| C466 | Humicola languinosa | Deuteromycete |
| C467 | Humicola grisea | Deuteromycete |
| C491 | Thielavia terrestris | Ascomycete |

TABLE 10

Screening of thermophilic fungi on solid medium for xylanase and cellulase activities*

| | Depth of clearing zone (mm) in various substrates | | |
|---|---|---|---|
| Fungal Strain | Aspenwood xylan | Aspenwood sawdust | Acid-swollen cellulose |
| A387 | 0 (1) | 3 (4) | 10 (3) |
| A435 | 26 (4) | 40 (2) | 40 (3) |
| B499 | 0 (1) | 0 (1) | 0 (1) |
| B508 | 28 (4) | 40 (4) | 9 (4) |
| B519 | 0 (1) | 0 (1) | 0 (1) |
| C341 | 34 (3) | 13 (4) | 13 (4) |
| C372 | 40 (2) | 16 (4) | 13 (4) |
| C375 | 40 (3) | 12 (4) | 4 (3) |
| C412 | 40 (3) | 40 (4) | 10 (4) |
| C416 | 0 (1) | 4 (4) | 0 (1) |
| C419 | 40 (2) | 40 (2) | 16 (4) |
| C424 | 40 (4) | 10 (4) | 10 (4) |
| C433 | 40 (2) | 4 (4) | 40 (2) |
| 235E | 40 (3) | 40 (3) | 10 (3) |
| C437 | 40 (3) | 0 (1) | 0 (1) |
| C463 | 0 (1) | 3 (3) | 4 (3) |
| C464 | 36 (3) | 10 (4) | 15 (4) |
| C465 | 24 (4) | 13 (4) | 13 (4) |
| C466 | 29 (4) | 0 (1) | 0 (1) |
| C467 | 40 (3) | 13 (4) | 4 (3) |
| C491 | 0 (1) | 0 (1) | 0 (1) |

*Cultures were grown in solid medium on various substrates and incubated at 45° C. for up to 4 weeks. Depth of clearing zone at 40 mm represents complete tube clearing. Values in parenthesis indicate the time of incubation (in weeks) when maximum tube clearing was observed.

TABLE 11

Production of xylanolytic and cellulolytic enzymes by thermophilic fungi in liquid culture*

| Fungal strain | Enzyme activities (IU/mL)*** | | | |
|---|---|---|---|---|
| | Xylanase | Endoglucanase | Filter Paper | B-glucosidase |
| A387 | 87.3 (7) | 12.20 | 0.47 | 0.18 |
| A435 | 1.6 (10) | 0.27 | 0.02 | 0.03 |
| A499 | 0.1 (3) | 0.06 | 0.02 | 0.03 |
| B508 | 12.4 (10) | 2.79 | 0.09 | 0.05 |
| B519 | n.d.** | n.d. | n.d. | n.d. |
| C341 | 20.3 (10) | 4.84 | 0.16 | 0.09 |
| C372 | 18.5 (5) | 3.40 | 0.16 | 0.15 |
| C375 | 3.3 (10) | 2.20 | 0.08 | 0.23 |
| C412 | 143.1 (10) | 7.30 | 0.22 | 0.47 |
| C416 | 0.8 (10) | 0.14 | 0.04 | 0.06 |
| C419 | 14.0 (7) | 6.56 | 0.18 | 0.38 |
| C424 | 11.0 (10) | 5.25 | 0.17 | 0.12 |
| C433 | 63.7 (7) | 8.50 | 0.67 | 0.40 |
| 235E | 365.8 (7) | 10.10 | 0.16 | 0.74 |
| C437 | 125.3 (10) | 7.78 | 0.29 | 0.04 |
| C463 | 6.1 (10) | 1.40 | 0.04 | 0.06 |
| C464 | 15.5 (5) | 4.77 | 0.17 | 0.21 |
| C465 | 5.8 (7) | 3.37 | 0.16 | 0.09 |
| C466 | n.d. | n.d. | n.d. | n.d. |
| C467 | 5.9 (10) | 4.38 | 0.44 | 0.07 |
| C491 | 0.1 (3) | 0.04 | 0.02 | 0.02 |

*Cultures were grown on Solka Floc (1%, w/v) in liquid Vogel's medium and incubated at 45° C. with shaking for up to 10 days.
**Not determined. Strains B519 and C466 did not show any visible growth under the present culture conditions.
***Enzyme activities listed were the maximum levels obtained. Values in parenthesis indicate the culture age at the time that maximum xylanase activity was detected in culture filtrates.

TABLE 12

Production of xylanolytic and cellulolytic enzymes by Thermoascus aurantiacus 235F grown on various cellulosic substrates in liquid medium

| Substrate (1%, w/v) | Enzyme Activities (IU/mL) | | | |
|---|---|---|---|---|
| | Xylanase | Endoglucanase | Filter Paper | B-glucosidase |
| A. Vogel's medium: | | | | |
| SEA-WI* | 98.2 (10)** | 2.87 | 0.16 | 0.31 |
| Sawdust | 40.5 (10) | 0.63 | 0.05 | 0.14 |
| Ball-milled Sawdust | 174.4 (10) | 5.62 | 0.27 | 1.34 |
| B. Mandel's medium: | | | | |
| Solka Floc | 94.6 (10) | 7.34 | 0.13 | 0.39 |
| SEA-WI | 62.6 (7) | 2.70 | 0.09 | 0.18 |
| Sawdust | 61.6 (10) | 0.91 | 0.05 | 0.16 |
| Ball-milled Sawdust | 80.7 (10) | n.d.*** | n.d. | n.d. |

*Water-insoluble residue of steam-exploded aspenwood.
**Enzyme activities listed were the maximum levels obtained. Values in parenthesis indicate the culture age at the time that maximum xylanase activity was detected in culture filtrates.
***Not determined.

The embodiments of the invention in which an exclusive property or privilege is claimed are defined as follows:

1. A process for the production of a thermally stable xylanase enzyme preparation having no significant cellulase enzyme activity, and suitable for the selective hydrolysis of hemicellulose in mixed cellulose and hemicellulose substrates, which process comprises culturing the 235E strain Thermoascus aurantiacus microorganism in a nutrient culture medium containing at least one cellulosic or hemicellulosic substrate;

separating from the culture medium a culture filtrate containing a major proportion of xylanase enzymes and a minor proportion of cellulase enzymes; and incubating the culture filtrate at a temperature of at least about 60° C. for a time sufficient to selectively inactivate the cellulase enzymes and recovering a culture filtrate having xylanase enzyme activity, but no significant cellulase enzyme activity.

2. The process of claim 1, wherein the culturing is effected at a temperature of at least 45° C.

3. The process of claim 2, wherein the culture medium contains cellulose pulp, oat-spelt xylan, steam treated aspenwood or sawdust as the substrate.

4. The process of claim 3, wherein the culture medium is Vogel's medium or Mandel's medium.

5. The process of claim 2, wherein the culturing is effected for a period of 5 to 12 days.

6. The process of claim 1, wherein the separation of the culture filtrate is effected by filtration or centrifugation.

7. The process of claim 1, wherein prior to incubating the culture filtrate at a temperature of at least about 60° C., said culture filtrate is concentrated by rotary evaporation.

8. The process of claim 1, wherein prior to incubating the culture filtrate at a temperature of at least about 60° C., said culture filtrate is concentrated by ultrafiltration through an ultrafiltration membrane having a low molecular weight cutoff point between 1,000 and 20,000 daltons to obtain a xylanase rich and cellulase rich retentate; and wherein the retentate is then incubated at a temperature of at least 60° C. to selectively inactivate the cellulase enzymes.

9. The process of claim 8, wherein the membrane has a low molecular weight cut-off point between 5,000 and 20,000.

10. The process of claim 8, wherein the membrane has a low molecular cut-off point between 5,000 and 15,000.

11. The process of claim 8, wherein the membrane has a low molecular cut-off point between 5,000 and 12,000.

12. The process of claim 8, wherein the membrane has a low molecular cut-off point between 5,000 and 10,000.

13. The process of claim 8, wherein the membrane is a non-cellulosic membrane.

14. The process of claim 8, wherein the membrane is a polysufone membrane.

* * * * *